United States Patent [19]

Rose et al.

[11] Patent Number: 5,683,971
[45] Date of Patent: Nov. 4, 1997

[54] ABRASIVE HAND CLEANING ARTICLE INCORPORATING WATERLESS HAND CLEANSER

[75] Inventors: Edward S. Rose, Leawood; Andrew V. Mike, Overland Park, both of Kans.; Raymond G. Wile, Liberty, Mo.

[73] Assignee: Dymon, Inc., Olathe, Kans.

[21] Appl. No.: 405,374

[22] Filed: Mar. 15, 1995

Related U.S. Application Data

[63] Continuation of Ser. No. 33,012, Mar. 18, 1993, abandoned.
[51] Int. Cl.⁶ .................. C11D 3/16; C11D 3/43
[52] U.S. Cl. .................. 510/130; 510/138; 510/143; 510/157
[58] Field of Search .................. 252/90, 91, 106, 252/162, 172, 173, 174.11, 176.21; 510/130, 131, 137, 138, 139, 140, 143, 157

[56] References Cited

U.S. PATENT DOCUMENTS

| | | | |
|---|---|---|---|
| Re. 31,885 | 5/1985 | Meitner | 252/91 |
| 3,277,013 | 10/1966 | Gianladis | 252/153 |
| 3,619,251 | 11/1971 | Stiles | 15/104.93 |
| 4,336,151 | 6/1982 | Like et al. | 252/106 |
| 4,448,704 | 5/1984 | Barby et al. | 252/91 |
| 4,665,580 | 5/1987 | Morris | 15/118 |
| 4,666,621 | 5/1987 | Clark et al. | 252/91 |
| 4,753,844 | 6/1988 | Jones et al. | 428/288 |
| 4,775,582 | 10/1988 | Abba et al. | 252/91 |
| 4,784,786 | 11/1988 | Smith et al. | 252/91 |
| 4,808,328 | 2/1989 | Flohr | 252/106 |
| 4,833,003 | 5/1989 | Win et al. | 252/91 |
| 4,853,281 | 8/1989 | Win et al. | |
| 4,927,556 | 5/1990 | Pokorny | 252/173 |
| 4,931,201 | 6/1990 | Julemont | 252/91 |
| 5,094,770 | 3/1992 | Sheridan et al. | 252/91 |
| 5,141,803 | 8/1992 | Pregozen | 428/288 |
| 5,234,719 | 8/1993 | Richter et al. | 427/384 |

FOREIGN PATENT DOCUMENTS

| | | |
|---|---|---|
| 0068722 | 1/1983 | European Pat. Off. . |
| 0256950 | 2/1988 | European Pat. Off. . |
| 0573277 | 12/1993 | European Pat. Off. . |
| 842866 | 7/1960 | United Kingdom . |
| 2179052 | 2/1987 | United Kingdom . |

OTHER PUBLICATIONS

Atlas Powder Company, Formulary of Typical Pharmacuetical Formulations For Topical Application Illustrating Use of ATLAS Surfactants and Sorbitol pp. 39–43.
Coleman, D–Limonene As a Degreasing Agent Nov., 1975 The Citrus Industry pp. 23–25.
P&G, Jergens Liquid Soap, Aug. 22, 1986 p. 1.
Lazorisak, Waterless Hand Cleaners and Barrier Creams, Apr. 1969 pp. 26, 28, 73.
Geoghegan Waterless Hand Cleaners, Aug. 1969 pp. 54–56, 82.

*Primary Examiner*—Glenn A. Caldarola
*Assistant Examiner*—Alexander G. Ghyka
*Attorney, Agent, or Firm*—Shook, Hardy & Bacon L.L.P.

[57] ABSTRACT

An abrasive hand cleaning article comprises a substrate presenting an abrasive surface and being capable of absorbing and retaining a fluid, and a nonabrasive aqueous hand cleanser absorbed in the substrate, the hand cleanser comprising one or both of a solvent and a surfactant whereby cleansing action is achieved by the solvent or surfactant, and abrasive cleansing action is achieved by the abrasive surface of the Substrate. The substrate can comprise a cloth-like towel. A plurality of such towels are provided in a continuous rolled cylinder which are housed in a selectively sealable, essentially airtight container. An opening in the lid of the container allows the user to remove individual towels which contain the appropriate amount of cleanser thereon.

10 Claims, No Drawings

ABRASIVE HAND CLEANING ARTICLE INCORPORATING WATERLESS HAND CLEANSER

This is a continuation of application Ser. No. 08/033,012 filed on Mar. 18, 1993 now abandoned.

BACKGROUND OF THE INVENTION

This invention relates in general to cleaning compositions, and, more particularly, to waterless hand cleaners.

Hand cleansing formulations typically contain a surfactant that solubilizes or emulsifies the soils present on the individual's skin or hands. These formulations inherently have soil-cleansing limitations when soil-emulsifiability or solvency alone is used as a cleaning mechanism. When only surfactants in combination with nonaggressive solvent cleansers are used in the cleansing compositions, the cleaning power of the composition may be inadequate when stubborn or embedded soils are present. If the chemical formula is too aggressive in terms of its solubilizing or emulsifying power, skin can be harmed due to defatting of the natural oils thereof, particularly when the cleanser is used repeatedly.

Many cleansing formulations which are currently available in the marketplace also contain abrasive particulates which mildly scour the skin surface to aid in the removal of embedded soils. Some examples of the abrasive particulates utilized are pumice, silica, and diatomaceous earth. These formulations can be of a "waterless" nature, a term indicating that water does not have to be added during the hand cleansing process. However, because this abrasive particulate is generally insoluble, it must be flushed away with water after the cleansing process to achieve residue-free hands, i.e., free of the fine abrasive particulate which would remain on the skin if not rinsed away.

After cleansing and rinsing, hands are often dried with a towel or cloth instead of air-drying for purposes such as speed and convenience, as well as to aid in mechanically removing any stubborn soils which remain on the skin. However, using a towel or cloth without using water to first rinse skin which has been cleaned with an abrasive hand cleanser will not effectively remove all residual abrasive materials from the skin.

Nonabrasive waterless hand cleansers which are currently commercially available have a gelatinous or paste-like high viscosity consistency. These cleansers often have both polar and nonpolar ingredients which are blended together to achieve removal of a wide variety of soils from the surface of the skin. The gelatinous surfactant which affords this type of waterless cleanser its gelatinous form also acts as a substrate to essentially permanently bind the emulsion of cleansing ingredients together. This gelatinous consistency has been essential for waterless hand cleansers in the past in order for them to achieve the continuous cleansing action necessary for the desired cleaning effectiveness due to extended contact between the cleanser and the skin, as the user can work and rework the cleanser on the skin in order to fully solubilize the soils until they are removed from the skin surface. If the cleanser were liquid instead of gelatinous, the necessary continuous cleansing action associated with waterless hand cleansers would not be achieved because the extended contact between the cleanser and the skin is not achieved. The lower viscosity of a liquid cleanser can also cause the cleanser to run off of the hands, thereby facilitating the potential waste of cleanser. Thus, the gelatinous or high viscosity nature of waterless hand cleansers has several advantages in comparison to liquid cleansers. One significant disadvantage associated with waterless hand cleansers is the need to use a towel or cloth or the like in order to remove excess cleanser from the skin. Another disadvantage, when abrasive particulates are incorporated into waterless hand cleansing formulations, is a need to rinse with water to assure total removal of insoluble abrasive particulates via mechanical flushing, when it is desirous to remove said particulates from the skin.

There is, therefore, a need to provide a waterless hand cleaning article having abrasive characteristics without the use of abrasive particulates, without a gelatinous surfactant, and without the need for an additional drying cloth or towel.

SUMMARY OF THE INVENTION

It is, therefore, an object of this invention to provide an abrasive hand cleaning article comprising a waterless hand cleanser which does not contain abrasive particles but which is incorporated onto an abrasive substrate so that cleansing of embedded soils can be achieved by the abrasive action of the substrate without the need for rinsing to remove a residue of abrasive particles from the skin.

It is also an object of this invention to provide a waterless hand cleansing composition in liquid form which is incorporated onto a towel or cloth-like substrate so that a gelatinous or paste-like surfactant is not required to act as a carrier-substrate, whereby no additional drying or wiping cloth is needed to remove the cleanser from the skin after the cleansing process.

It is a further object of the present invention to provide an abrasive hand cleaning article comprising a waterless hand cleanser in liquid form incorporated onto a towel or cloth-like substrate so that extended contact between the cleanser and the skin can be achieved during the cleansing process, thereby enhancing the efficiency and cleansing capabilities of the cleanser due to the continuous cleaning effect provided.

It is yet another object of the present invention to provide an abrasive hand cleaning article comprising a liquid cleanser whereby strong cleansing action is achieved without the need for harsh chemical formulas which can harm the skin.

To accomplish these and other related objects of the invention, an abrasive hand cleaning article is provided comprising a substrate, such as a cloth-like towel, presenting an abrasive surface and being capable of absorbing and retaining a fluid, and a nonabrasive aqueous waterless hand cleanser absorbed in the substrate, said hand cleanser comprising one or both of a solvent and a surfactant, whereby cleansing action is achieved by the solvent or surfactant and abrasive cleansing action is achieved by the abrasive surface of the substrate. The article further comprises a plurality of towels provided in a continuous rolled cylinder housed in a sealed container, the axis of the cylinder being aligned in an essentially vertical orientation within the container, and a lid associated with the container and having an opening for receiving the towels therethrough. A preferred embodiment of the aqueous hand cleanser comprises 2–40% by weight of an organic solvent, 2–20% by weight of a surfactant, and 60–95% by weight water.

DESCRIPTION OF THE PREFERRED EMBODIMENT(S)

A hand cleaning article is provided comprising an abrasive substrate and a waterless hand cleanser incorporated thereon. The abrasive substrate of the preferred embodiment comprises a cloth-like towel similar to that described in U.S. Pat. No. 4,833,003 to Kimberly-Clark entitled "Uniformly Moist Abrasive Wipes," issued May 23, 1989, which is herein incorporated by reference in its entirety. The towel encompassed within the scope of this invention has two opposed surfaces, with an abrasive ingredient being permanently attached to or an integral part of at least one surface thereof, although it is possible for the abrasive ingredient to be present on both surfaces of the towel. The abrasive ingredient comprises a surface texture which enables the towel to produce a mild scrubbing action on the skin in order to remove embedded soils, while not harming the skin by scratching or the like. The abrasive towel as set forth in the referenced patent is made from non-woven material and comprises an abrasive surface layer that is thermally bonded to a melt blown supporting web. The abrasive surface is formed by melt blown fibers and irregular shaped polymeric globules having a diameter of at least 40 micrometers. The material has a high absorbency as a result of pores having a size of 20 to 60 microns. The preferred material is polypropylene. It is to be understood, of course, that the present invention is not specifically limited to the abrasive material disclosed in the referenced patent. To be optimally effective, the abrasive ingredient of this invention can account for a minimum of 10% and a maximum of 90% of the surface area of the abrasive side of the towel, with the remaining side having a smooth surface for wiping. It is anticipated that both sides of the towel can have abrasive ingredients incorporated thereon, and that the percentage of abrasive ingredient on each side can differ as desired.

In addition, the towel must be capable of absorbing and retaining a predetermined amount of fluid, such as the aqueous cleansing formulation which is associated herewith, sufficient to provide a uniformly moist towel. The absorbent character of the towel encompassed herein is achieved by a system of voids or pores which absorb and tightly retain the aqueous formulation, such as by capillary action. The towel should also be capable of readily releasing the liquid during use. The specific void or pore volume of the structure of the towel regulates the amount of fluid which can be retained in the towel.

The waterless hand cleanser which is incorporated onto the towel is an aqueous formulation capable of removing a variety of soils from the skin. This aqueous formulation has a viscosity sufficient for being easily absorbed into the pores or voids of the towel through capillary action. The waterless hand cleanser of a preferred embodiment comprises: 2–40% by weight of organic solvents; 2–20% by weight of a surfactant; 40–96% by weight of a carrier; and 0–3% by weight inert ingredients. The solvent is preferably one capable of solubilizing greasy, oily soils, such as aliphatic solvents, dibasic esters, petroleum oils, vegetable oils, alcohols, glycols, glycol ethers, furfuryls, petroleum distillates and polyols. The surfactant preferably is nonionic, anionic or amphoteric to promote water/oil single-phase emulsion of ingredients, and to emulsify and suspend solvents. The carrier comprises a nonflammable vehicle which also acts as a solvent for water-soluble soils. The inert ingredients may include fragrances, preservatives, emollients, antioxidants, and microbicidal agents.

An example of a preferred formulation embodied by this invention is as follows, with both the preferred and the acceptable ranges of ingredients being indicated:

| INGREDIENT | PREFERRED % BY WEIGHT | ACCEPTABLE RANGE OF % |
|---|---|---|
| 1. d-Limonene | 9.50 | 1.00–20.00 |
| 2. Odorless Mineral Spirits | 4.70 | 1.00–20.00 |
| 3. Lemon 1061 | 0.05 | 0.01–0.50 |
| 4. Tergitol\15-S-5 | 3.00 | 1.00–10.00 |
| 5. Water | 77.10 | 60.00–95.00 |
| 6. Sodium Lauryl Sulfate | 4.00 | 1.00–10.00 |
| 7. Preservative | 0.30 | 0.10–0.50 |
| 8. Potassium Sorbate | 0.20 | 0.10–0.50 |
| 9. Sorbitol | 1.00 | 0.50–5.00 |
| 10. BHT | 0.05 | 0.01–1.00 |
| 11. Bactericide | 0.10 | 0.01–0.50 |

Tergitol\ 15-S-5 is a trademark for a nonionic surfactant.

This aqueous emulsion formulation includes both ionic and nonionic ingredients to emulsify and suspend a variety of soils, as well as skin emollients and bactericides and antifungus/mold agents. Previously, such a waterless hand cleansing formulation has required as an additional ingredient a gelatinous-forming surfactant to act as a substrate or matrix to bind the ionic and nonionic ingredients together in an essentially permanent suspension. Notably, the gel-forming surfactant of the prior art is not required in this invention, as the towel itself acts as a substrate or matrix to hold the ingredients of the cleansing formulation in suspension.

In preparing the hand cleaning article of a preferred embodiment, a plurality of abrasive towels are provided, preferably in a continuous, perforated, rolled cylinder of towels. The line of perforation presents a line of weakness by which said towels can be easily separated. Said towels are inserted on-end into a selectively resealable, preferably cylindrical container, with the axis of the cylinder being aligned in an essentially vertical orientation. Of course, it is anticipated that an alternative preferred embodiment of this invention could provide a stack of individual towels instead of the continuous cylinder or roll of towels. The aqueous formulation is then added to the container, preferably by pouring the same over the cylinder of towels, thereby moistening the towels with the cleansing formulation within the container. The capillary action associated with the void volume of the towel as discussed above causes the aqueous cleansing formulation to be evenly distributed throughout the cylinder of towels.

An example of a suitable container for holding the towels comprises an essentially airtight lid on the top portion thereof which can be selectively sealed, said lid comprising a hinged cap having an opening positioned thereunder. This opening allows for the passage of towels from the interior of the sealed container via the opening, whereby individual towels can be removed from the interior cylinder by pulling the towel and tearing the same off of the cylinder at the perforated line located between each individual towel. The opening is appropriately sized to provide means for removing excess liquid from each individual towel as it is removed from the container.

In use, an individual towel is removed from the container as described above. When properly prepared, the towel contains an amount of cleanser sufficient to thoroughly cleanse the skin of the user. As the towel is rubbed on the skin, it releases the liquid cleanser and allows it to have extended contact time with the skin, and also provides for continuous cleansing without the need to apply additional cleanser. The abrasive character of the towel facilitates removal of embedded soils without leaving any abrasive residue on the skin, which residue would otherwise necessitate rinsing the skin with water after the cleansing process to thoroughly remove said abrasive residue. Thus, a waterless hand cleaner article is provided without the negative features associated with the conventional waterless hand cleaners of the prior art.

The hand cleaner of the present invention also assures efficient use of the cleanser, as the proper amount of cleanser is provided for each individual use. Other low viscosity liquid cleansers tend to be wasted as the low viscosity associated with such cleansers often causes them to run off of the skin. Gelatinous cleansers are also difficult to use efficiently, as the user often utilizes too little, necessitating a repeated application, or too much, requiring a cloth or towel to remove the wasted excess.

Furthermore, the towel of the present invention acts not only as a substrate for the cleansing formulation and as a vehicle for the abrasive ingredient, but it also works to dry the skin after the cleanser has been used and has partially evaporated from the towel.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. An abrasive hand cleaning article comprising:
   a substrate presenting two opposed surfaces, and having an abrasive ingredient permanently forming a part of at least one said surface, said substrate presenting a matrix capable of absorbing and retaining other components therein; and
   a waterless hand cleanser emulsion absorbed in the substrate and retained by said matrix, said emulsion comprising:
   2–40% by weight of an emulsifiable organic solvent non-irritable to human skin and capable of solubilizing greasy, oily soils and comprising one or more of an aliphatic liquid, a dibasic ester, vegetable oil, terpene, and a glycol ether;
   2–20% by weight of a surfactant characterized by the ability to form a water and oil emulsion with said solvent; and
   60–95% by weight of water;
   whereby said substrate maintains its abrasive quality in the presence of said emulsion and an abrasive cleansing action is achieved by the combination of said emulsion and the abrasive ingredient on the surface of said substrate.

2. An abrasive hand cleaning article as set forth in claim 1, wherein said substrate comprises a towel.

3. An abrasive hand cleaning article as set forth in claim 2, wherein said towel presents two (2) abrasive surfaces.

4. An abrasive hand cleaning article as set forth in claim 1, wherein said solvent comprises:
   1–20% by weight d-Limonene; and
   1–20% by weight mineral spirits.

5. An abrasive hand cleansing article as set forth in claim 4, wherein said surfactant comprises 1–20% by weight of a nonionic surfactant.

6. An abrasive hand cleaning article as set forth in claim 1, wherein
   said solvent comprises 1–20% by weight d-Limonene and 1–20% by weight mineral spirits;
   said surfactant comprises 2–20% by weight nonionic surfactant;
   and said emulsion further comprises:
   0.1–0.5% by weight fungicide/mildewcide;
   0.5–0.5% by weight skin emollient;
   0.01–1% by weight antioxidant; and
   0.11–1.0% by weight bacterial agent.

7. An abrasive hand cleaning article comprising:
   a substrate comprising a towel presenting two opposed surfaces, and having an abrasive ingredient permanently forming a part of at least one said surface, said substrate presenting a matrix capable of absorbing and retaining other components therein;
   a nonabrasive, waterless hand cleanser emulsion absorbed in the towel, said emulsion comprising:
   2–40% by weight of an emulsifiable organic solvent non-irritable to human skin and capable of solubilizing greasy, oily soils and comprising one or more of an aliphatic liquid, a dibasic ester, vegetable oil, terpene, and a glycol ether;
   2–20% by weight of a surfactant characterized by the ability to form a water and oil emulsion with said solvent; and
   60–95% by weight of water;
   whereby said substrate maintains its abrasive quality in the presence of said emulsion and an abrasive cleansing action is achieved by the combination of said emulsion and the abrasive ingredient on the surface on said towel;
   a plurality of said towels being provided in a continuous rolled cylinder, separated at a line of perforation between each said towel; and
   a selectively sealable, essentially airtight container having a hollow interior in which said cylinder of towels are housed, the axis of said cylinder being aligned in an essentially vertical orientation within said container, and a lid associated therewith, said lid comprising an opening therein for receiving said towels therethrough, said opening having a selectively closeable cap associated therewith,
   whereby an individual said towel incorporating said emulsion can be removed from the interior of said container through said opening, and separated from the cylinder by tearing along the line of perforation.

8. A method for preparing a hand cleaning article, said method comprising:
   providing a plurality of towels in a continuous rolled cylinder separated by a line of perforation, said towels presenting two opposed surfaces, and having an abrasive ingredient permanently forming a part of at least one said surface, said towel being capable of absorbing and retaining fluid while maintaining its abrasive quality;
   providing a non-abrasive, waterless hand cleanser emulsion incorporated onto said towel, said emulsion comprising:
   2–40% by weight of an emulsifiable organic solvent non-irritable to human skin and capable of solubilizing greasy, oily soils and comprising one or more of an aliphatic liquid, a dibasic ester, vegetable oil, terpene, and a glycol ether;

2–20% by weight of a surfactant characterized by the ability to form a water and oil emulsion with said solvent; and 60–95% by weight of water;

providing a selectively sealable container having a hollow interior in which said cylinder of towels are housed, said container having a lid with an opening therewith, and a selectively closeable cap associated therewith;

placing said cylinder of towels into the interior of said container with the axis of the cylinder aligned in an essentially vertical orientation;

adding said emulsion to said cylinder of towels in said container to thereby appropriately moisten said towels with a predetermined amount of said emulsion; and sealing said lid on said container to provide an essentially airtight container.

9. An abrasive hand cleaning article comprising:

a substrate comprising a towel presenting two opposed surfaces, and having an abrasive ingredient permanently forming a part of at least one said surface, said surface presenting a matrix capable of absorbing and retaining other components therein;

a nonabrasive, waterless hand cleanser emulsion comprising 1–20% by weight d-Limonene, 1–20% by weight mineral spirits, 60–95% by weight water, 2–20% by weight nonionic surfactant, 0.1–0.5% by weight fungicide/mildewcide 0.5–5% by weight skin emollient, 0.01–1% by weight antioxidant, and 0.11–1.0% by weight bacterial agent, said emulsion being absorbed in the towel, whereby cleansing action is achieved by the combination of said emulsion and the abrasive ingredient on the surface on said towel and whereby said substrate maintains its abrasive quality in the presence of said emulsion;

a plurality of said towels being provided in a continuous rolled cylinder, separated at a line of perforation between each said towel; and a selectively sealable, essentially airtight container having a hollow interior in which said cylinder of towels is housed, the axis of said cylinder being aligned in an essentially vertical orientation within said container, and a lid associated therewith, said lid comprising an opening therein for receiving said towels therethrough, said opening having a electively closeable cap associated therewith, whereby an individual said-towel incorporating said emulsion can be removed from the interior of said container through said opening, and separated from the cylinder by tearing along the line of perforation.

10. An abrasive hand cleaning article as set forth in claim 1, wherein:

said solvent comprises d-Limonene and mineral spirits, said d-Limonene being present in the amount of approximately 9.5% by weight, and said mineral spirits being present in the amount of approximately 4.7% by weight;

said water is present in the amount of approximately 77.1%: by weight;

said surfactant comprises a nonionic surfactant which is present in the amount of approximately 7% by weight; and said emulsion further comprises:
approximately 0.2% by weight fungicide/mildewcide;
approximately 1% by weight skin emollient;
approximately 0.05% by weight antioxidant; and
approximately 0.4% by weight bacterial agent.

\* \* \* \* \*

REEXAMINATION CERTIFICATE (4188th)

United States Patent [19]

Rose et al.

[11] B1 5,683,971

[45] Certificate Issued Oct. 24, 2000

[54] ABRASIVE HAND CLEANING ARTICLE INCORPORATING WATERLESS HAND CLEANSER

[75] Inventors: Edward S. Rose, Leawood; Andrew V. Mike, Overland Park, both of Kans.; Raymond G. Wile, Liberty, Mo.

[73] Assignee: Dymon, Inc., Olathe, Kans.

Reexamination Request:
No. 90/005,600, Dec. 29, 1999

Reexamination Certificate for:
Patent No.: 5,683,971
Issued: Nov. 4, 1997
Appl. No.: 08/405,374
Filed: Mar. 15, 1995

Related U.S. Application Data

[63] Continuation of application No. 08/033,012, Mar. 18, 1993, abandoned.

[51] Int. Cl.[7] .................................. C11D 3/16; C11D 3/43

[52] U.S. Cl. .......................... 510/130; 510/138; 510/143; 510/157

[56] References Cited

U.S. PATENT DOCUMENTS

| | | | |
|---|---|---|---|
| 4,659,609 | 4/1987 | Lamers et al. | 428/194 |
| 5,063,062 | 11/1991 | Greenspan et al. | 424/443 |

*Primary Examiner*—Charles Bowers, Jr.

[57] ABSTRACT

An abrasive hand cleaning article comprises a substrate presenting an abrasive surface and being capable of absorbing and retaining a fluid, and a nonabrasive aqueous hand cleanser absorbed in the substrate, the hand cleanser comprising one or both of a solvent and a surfactant whereby cleansing action is achieved by the solvent or surfactant, and abrasive cleansing action is achieved by the abrasive surface of the Substrate. The substrate can comprise a cloth-like towel. A plurality of such towels are provided in a continuous rolled cylinder which are housed in a selectively sealable, essentially airtight container. An opening in the lid of the container allows the user to remove individual towels which contain the appropriate amount of cleanser thereon.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–10 is confirmed.

\* \* \* \* \*